United States Patent
Bowe et al.

(10) Patent No.: US 7,717,899 B2
(45) Date of Patent: May 18, 2010

(54) INNER AND OUTER TELESCOPING CATHETER DELIVERY SYSTEM

(75) Inventors: Wade A. Bowe, Temecula, CA (US); Eric Johnson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1637 days.

(21) Appl. No.: 10/059,809

(22) Filed: Jan. 28, 2002

(65) Prior Publication Data

US 2003/0144657 A1     Jul. 31, 2003

(51) Int. Cl.
*A61M 25/00* (2006.01)
(52) U.S. Cl. .................. 604/525; 600/585; 604/95.04
(58) Field of Classification Search ........... 604/95.01, 604/95.04, 158, 159, 161, 530, 532, 523–528, 604/164.01, 164.03; 600/585; 606/41
See application file for complete search history.

(56) References Cited

U.S. PATENT DOCUMENTS

| | | | |
|---|---|---|---|
| 4,033,331 A | | 7/1977 | Guss et al. |
| 4,516,972 A | * | 5/1985 | Samson .................. 604/526 |
| 4,777,951 A | | 10/1988 | Cribier et al. |
| 4,787,884 A | | 11/1988 | Goldberg |
| 4,898,577 A | | 2/1990 | Badger et al. |
| 4,976,689 A | | 12/1990 | Buchbinder et al. |
| 4,986,814 A | | 1/1991 | Burney et al. |
| 5,007,434 A | | 4/1991 | Doyle et al. |
| 5,030,204 A | | 7/1991 | Badger et al. |
| 5,067,946 A | | 11/1991 | Zhadanov |
| 5,109,830 A | | 5/1992 | Cho |
| 5,114,414 A | | 5/1992 | Buchbinder |
| 5,222,949 A | | 6/1993 | Kaldany |
| 5,279,596 A | | 1/1994 | Castaneda et al. |
| 5,290,229 A | * | 3/1994 | Paskar .................. 604/95.04 |
| 5,304,131 A | | 4/1994 | Paskar |
| 5,308,342 A | | 5/1994 | Sepetka et al. |
| 5,318,528 A | | 6/1994 | Heaven et al. |
| 5,376,074 A | | 12/1994 | Buchbinder et al. |
| 5,389,090 A | | 2/1995 | Fischell et al. |
| 5,397,304 A | | 3/1995 | Truckai |
| 5,423,772 A | | 6/1995 | Lurie et al. |
| 5,423,773 A | | 6/1995 | Jimenez |

(Continued)

FOREIGN PATENT DOCUMENTS

DE     3819372     1/1990

(Continued)

*Primary Examiner*—Nicholas D Lucchesi
*Assistant Examiner*—Theodore J Stigell
(74) *Attorney, Agent, or Firm*—Faegre & Benson LLP

(57) ABSTRACT

A catheter assembly employs an outer catheter with a pre-formed distal end and an open lumen. An inner catheter having an open lumen and a pre-formed distal end is movably disposed within the outer catheter. Relative rotation and extension of the inner and outer catheters provides the distal end of the catheter assembly with an adjustable range of two- and three-dimensional shapes. The inner catheter can include sections of varying stiffness, such that extension of the inner catheter within the outer catheter modifies the shape of the outer catheter's pre-formed distal end. The adjustable shaping of the catheter assembly's distal tip provides an improved system for locating and cannulating cardiac venous structures, particularly the coronary sinus via the right atrium.

26 Claims, 10 Drawing Sheets

U.S. PATENT DOCUMENTS

| | | | |
|---|---|---|---|
| 5,445,624 A | 8/1995 | Jimenez | |
| 5,487,757 A | 1/1996 | Truckai et al. | |
| 5,488,960 A | 2/1996 | Toner | |
| 5,497,784 A | 3/1996 | Imran | |
| 5,533,985 A | 7/1996 | Wang | |
| 5,542,935 A | 8/1996 | Unger et al. | |
| 5,545,200 A | 8/1996 | West et al. | |
| 5,569,218 A | 10/1996 | Berg | |
| 5,611,777 A | 3/1997 | Bowden et al. | |
| 5,626,602 A | 5/1997 | Gianotti et al. | |
| 5,632,734 A | 5/1997 | Galel et al. | |
| 5,651,785 A | 7/1997 | Abela et al. | |
| 5,658,263 A | 8/1997 | Dang et al. | |
| 5,676,653 A | 10/1997 | Taylor | |
| 5,758,562 A | 6/1998 | Thompson | |
| 5,762,637 A | 6/1998 | Berg | |
| 5,775,327 A | 7/1998 | Randolph et al. | |
| 5,782,239 A | 7/1998 | Webster, Jr. | |
| 5,785,689 A | 7/1998 | de Toledo et al. | |
| 5,814,029 A | 9/1998 | Hassett | |
| 5,868,700 A | 2/1999 | Voda | |
| 5,868,741 A | 2/1999 | Chia et al. | |
| 5,882,333 A | 3/1999 | Schaer et al. | |
| 5,899,890 A | 5/1999 | Chiang et al. | |
| 5,902,289 A | 5/1999 | Swartz et al. | |
| 5,906,590 A | 5/1999 | Hunjan et al. | |
| 5,911,715 A | 6/1999 | Berg et al. | |
| 5,911,725 A | 6/1999 | Boury | |
| 5,935,102 A | 8/1999 | Bowden et al. | |
| 5,935,160 A | 8/1999 | Auricchio et al. | |
| 5,984,957 A | 11/1999 | Laptewicz, Jr. et al. | |
| 6,021,340 A | 2/2000 | Randolph et al. | |
| 6,066,126 A | 5/2000 | Li et al. | |
| 6,086,548 A | 7/2000 | Chaisson et al. | |
| 6,090,084 A | 7/2000 | Hassett et al. | |
| 6,093,177 A | 7/2000 | Javier, Jr. et al. | |
| 6,110,163 A | 8/2000 | Voda | |
| 6,122,552 A | 9/2000 | Tockman et al. | |
| 6,165,163 A * | 12/2000 | Chien et al. | 604/523 |
| 6,165,167 A | 12/2000 | Delaloye | |
| 6,241,726 B1 | 6/2001 | Raymond Chia et al. | |
| 6,251,092 B1 | 6/2001 | Qin et al. | |
| 6,251,104 B1 | 6/2001 | Kesten et al. | |
| 6,277,107 B1 | 8/2001 | Lurie et al. | |
| 6,280,433 B1 | 8/2001 | McIvor et al. | |
| 6,280,456 B1 | 8/2001 | Scribner et al. | |
| 6,308,091 B1 | 10/2001 | Avitall | |
| 6,322,548 B1 | 11/2001 | Payne et al. | |
| 6,408,214 B1 * | 6/2002 | Williams et al. | 607/122 |
| 6,471,678 B1 | 10/2002 | Alvarez de Toledo et al. | |
| 6,475,195 B1 | 11/2002 | Voda | |
| 6,511,471 B2 | 1/2003 | Rosenman et al. | |
| 6,526,302 B2 | 2/2003 | Hassett | |
| 6,530,914 B1 | 3/2003 | Mickley | |
| 6,537,253 B1 | 3/2003 | Haindl | |
| 6,558,368 B1 | 5/2003 | Voda | |
| 6,592,581 B2 | 7/2003 | Bowe | |
| 6,623,449 B2 | 9/2003 | Paskar | |
| 6,638,268 B2 * | 10/2003 | Niazi | 604/528 |
| 6,676,637 B1 | 1/2004 | Bonnette et al. | |
| 6,706,018 B2 | 3/2004 | Westlund et al. | |
| 6,716,207 B2 | 4/2004 | Farnholtz | |
| 6,755,812 B2 | 6/2004 | Peterson et al. | |
| 6,852,261 B2 | 2/2005 | Benjamin | |
| 6,869,414 B2 | 3/2005 | Simpson et al. | |
| 6,902,555 B2 * | 6/2005 | Paskar | 604/500 |
| 6,953,454 B2 | 10/2005 | Peterson et al. | |
| 7,089,063 B2 | 8/2006 | Lesh et al. | |
| 7,493,156 B2 | 2/2009 | Manning et al. | |
| 2001/0005783 A1 | 6/2001 | Hassett | |
| 2001/0039413 A1 * | 11/2001 | Bowe | 604/532 |
| 2001/0052345 A1 | 12/2001 | Niazi | |
| 2002/0026175 A1 | 2/2002 | Paskar | |
| 2002/0188278 A1 | 12/2002 | Tockman et al. | |
| 2003/0004537 A1 | 1/2003 | Boyle et al. | |
| 2003/0130598 A1 | 7/2003 | Manning et al. | |

FOREIGN PATENT DOCUMENTS

| | | |
|---|---|---|
| GB | 2025233 | 1/1980 |
| JP | 60-21767 | 2/1985 |
| WO | WO 99/55412 | 4/1999 |

* cited by examiner

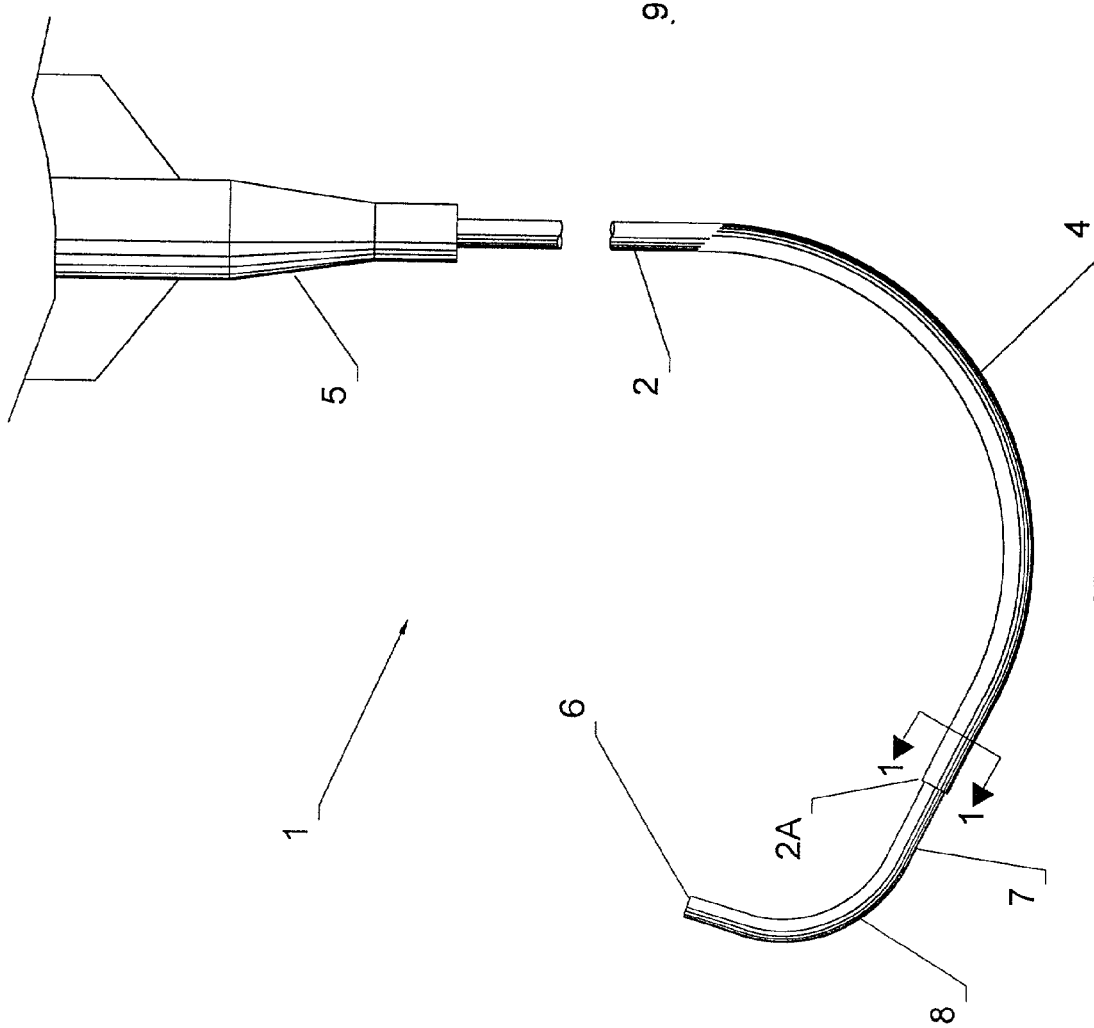

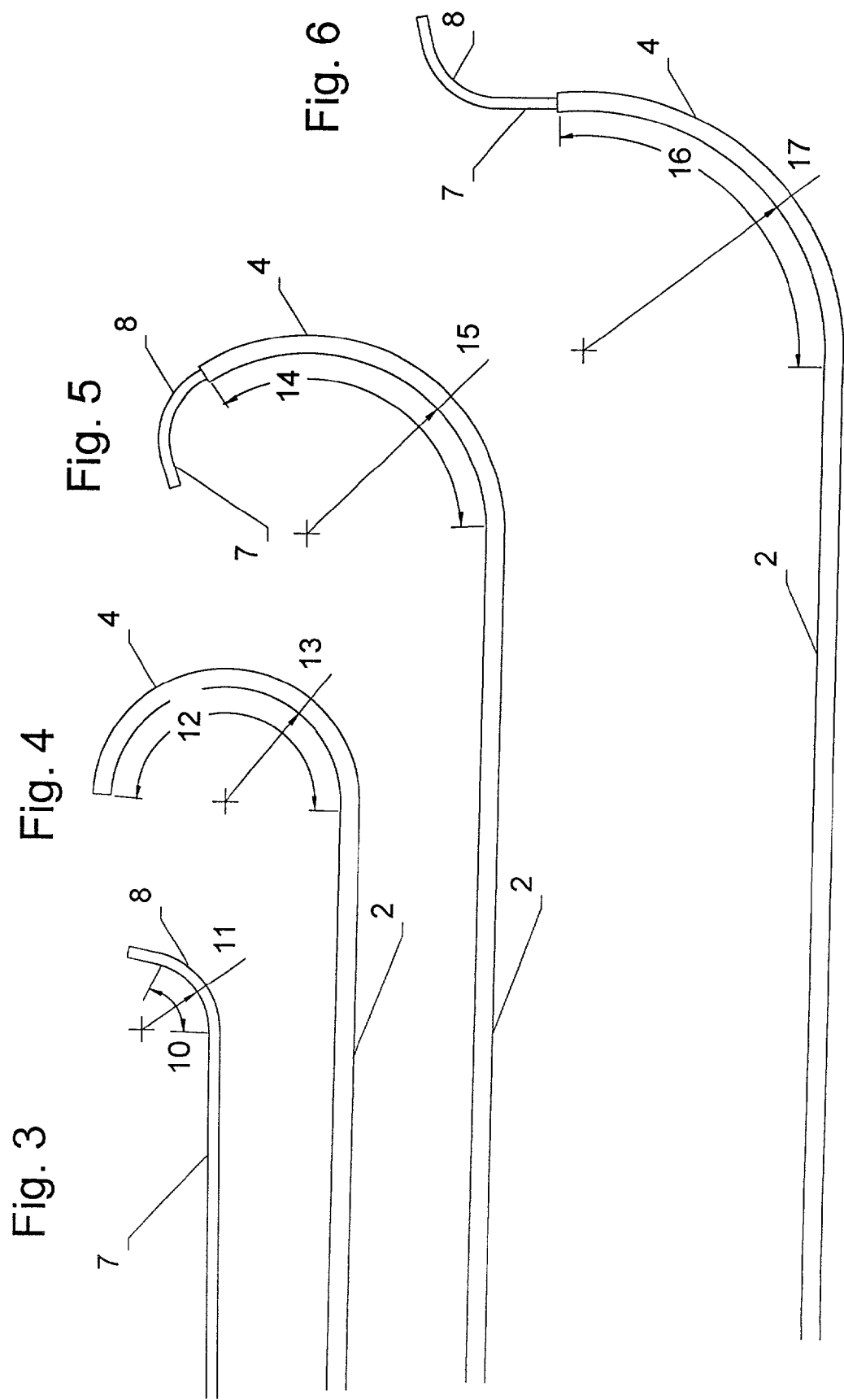

Section 2-2

Section 3-3

INNER AND OUTER TELESCOPING CATHETER DELIVERY SYSTEM

FIELD OF THE INVENTION

The invention relates generally to guiding catheters, and more particularly to dual-sheath telescoping guiding catheters used to locate and cannulate the coronary sinus of a patient's heart.

BACKGROUND OF THE INVENTION

Guiding catheters are instruments that allow a physician to access and cannulate vessels in a patient's heart for conducting various medical procedures, including venography and implanting of cardiac pacing devices. Cannulating heart vessels often requires navigating a small diameter, flexible guide through the convoluted vasculature into a heart chamber, and then into a destination heart vessel. Once the destination heart vessel is reached, the catheter acts as a conduit for insertion of payloads into the heart vessel.

A commonly accessed destination vessel for cardiac pacing lead insertion is the coronary sinus. A pre-shaped guiding catheter is typically used to blindly locate the coronary sinus ostium, but this endeavor is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized unipolar or bipolar waveforms) using an electrophysiological (EP) catheter and an ECG monitor. After the ostium is located, the guiding catheter can be used to inject radiographic contrast media into the coronary sinus to highlight the associated venous system, and then a pacing lead is installed within one of the coronary branches.

Complicating this scenario is the dynamic structural deformation of the heart chambers that occurs from normal cardiac activity during the procedure. This further increases the difficulty of guiding a catheter to its destination. Presently, a considerable amount of time is often spent by the physician when manipulating such catheters within cardiac structures, such as the right atrium, simply trying to locate an anatomical feature of interest, such as the coronary sinus ostium.

Guiding catheter systems are typically configured with a profile that is optimized for the intended method of access. In the case of accessing the coronary sinus via the right atrium, a catheter with a distal contour including a relatively sharp bend will point the catheter towards the likely location of the coronary sinus once the right atrium is reached. The contours of pre-shaped guiding catheters are generally fixed, and this is typically achieved in production by constraining the distal end within a shaping fixture while warming them until they assume the intended shape (i.e., by "heat setting" their polymer shaft).

A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. Fixed shape catheters may require a time consuming trial and error process of inserting and removing different shapes until the destination vessel is successfully accessed.

Steerable catheters are also used for various guiding applications. Steerable catheters typically rely on an integral steering mechanism that includes a mechanical linkage to a deflection point at the catheter's distal end. These devices can be effective in allowing dynamic reshaping of the catheter's distal end, however they are not ideal for all situations. The linkage takes up space within the catheter's lumen, leaving less space within the catheter for payloads. The linkage usually has some clearance within the lumen to allow for easier longitudinal movement of the linkage. The clearance can result in backlash when the steering mechanism is operated. Depending on the length and deployed shape of the catheter, backlash of a steered catheter may render it difficult to operate.

There is a need for an improved guiding catheter having a simple means of adjusting the distal end shape for venous access and cannulation. There exists a further need for a guiding catheter that provides an adjustable distal end shape while maximizing available payload space within the guiding catheter. The present invention fulfills these and other needs, and addresses other deficiencies of prior art implementations.

SUMMARY OF THE INVENTION

The present invention is directed to a catheter assembly for cannulating the coronary sinus of a patient's heart accessed from the right atrium. According to one embodiment of the present invention, the catheter assembly includes an outer catheter having an open lumen and a pre-formed distal end. An inner catheter having an open lumen and a pre-formed distal end is movably disposed within the open lumen of the outer catheter. The pre-formed distal end of the inner catheter is more flexible than the distal end of the outer catheter. The catheter assembly includes a proximal mechanism used for axially rotating the outer catheter relative to the inner catheter and longitudinally translating the inner catheter relative to the outer catheter. The axial rotation and longitudinal translation allows the distal end of the catheter assembly to assume a selectable plurality of two- and three-dimensional shapes appropriate for accessing the coronary sinus or other vessel of interest.

In another embodiment, the pre-formed distal end of the inner catheter further includes at least two adjacent longitudinal sections of varying stiffness, and a stiffness transition region between the sections of varying stiffness. In this embodiment, the shape of the pre-formed distal end of the outer catheter is changed by relative longitudinal translation between the outer and inner catheters, thereby changing orientation of the sections of varying stiffness of the inner catheter relative to the pre-formed distal end of the outer catheter.

In one configuration of the catheter according to the present invention, the pre-formed distal end of the outer catheter further includes at least two adjacent longitudinal sections of varying stiffness. The outer catheter of this configuration further includes a stiffness transition region between the adjacent longitudinal sections of varying stiffness on the outer catheter.

The pre-formed distal end of the inner catheter may be tapered. The distal end of the inner catheter typically protrudes from the distal end of the outer catheter. In one configuration, the distal end of the inner catheter protrudes from about 3 cm to about 15 cm from a distal tip of the outer catheter. The pre-formed distal end of the inner catheter may include a bend having a bend radius ranging from about 0.5 cm to about 5.0 cm and a bend angle ranging from about 0 degrees to about 180 degrees.

One useful shape of the pre-formed distal end of the outer catheter includes a first straight section at the distal tip of the outer catheter having a length of about 0 cm to about 6 cm. A first curve is proximally adjacent to the first straight section and has a bend radius of about 1 cm to about 5 cm and a bend angle of about 0 degrees to about 80 degrees. A second straight section is proximally adjacent to the first curve and has a length of about 0 cm to about 6 cm. A second curve is proximally adjacent to the second straight section and has a bend radius of about 1 cm to about 5 cm and a bend angle of about 0 degrees to about 100 degrees.

In some configurations, a third straight section is proximally adjacent to the second curve and has a length of about 0 cm to about 6 cm. A third curve can then be proximally adjacent to the third straight section and have a bend radius of about 1 cm to about 5 cm and a bend angle of about 0 degrees to about 125 degrees.

A catheter assembly according to the present invention may further include a steering mechanism disposed within the open lumen of the inner catheter. The steering mechanism has a guide member and a pull wire. The guide member and the pull wire are extendable beyond the pre-formed distal end of the inner catheter. A bend at a distal section of the guide member is developed upon application of a force to the pull wire. The distal end of the catheter assembly can assume a plurality of two- and three-dimensional shapes in response to application of the force to the pull wire, as well as axial rotation and longitudinal translation of the outer catheter relative to the inner catheter.

In one configuration, the guide member includes a guide wire. In another configuration, the guide member includes a guide ribbon. The inner catheter may further include longitudinal slots disposed along the open lumen of the inner catheter. The guide ribbon in such a configuration is slidably disposed within the longitudinal slots of the inner catheter.

The catheter assembly may include at least one electrode located on the distal end of at least one of the inner and outer catheters. Such an arrangement further includes at least one electrical conductor coupled to the electrode(s), the conductor disposed within at least one of the inner and outer catheters.

In yet another embodiment of the present invention, the catheter assembly further includes an occlusion balloon connected to the distal end of the inner catheter and/or the distal end of the outer catheter.

According to another embodiment of the present invention, a method of inserting a guiding catheter into a coronary sinus of a patient's heart involves providing a catheter assembly, the catheter assembly including an outer catheter, an inner catheter and a proximal mechanism. The outer catheter includes an open lumen and a pre-formed distal end. The inner catheter includes an open lumen and a pre-formed distal end, and the inner catheter is movably disposed within the open lumen of the outer catheter. The pre-formed distal end of the inner catheter is more flexible than the distal end of the outer catheter. The proximal mechanism provides for axially rotating the outer catheter relative to the inner catheter and longitudinally translating the inner catheter relative to the outer catheter. An orientation of the pre-formed distal end of the outer catheter relative to the pre-formed distal end of the inner catheter is modified by relative axial rotation and relative longitudinal translation between the outer and inner catheters such that a distal end of the catheter assembly can assume a selectable plurality of two- and three-dimensional shapes appropriate for accessing the coronary sinus or other vessel of interest.

The method further involves inserting the distal end of the catheter assembly through a patient's right atrium via an access vessel. The outer catheter is axially rotated relative to the inner catheter and the inner catheter is longitudinally displaced relative to the outer catheter using the proximal mechanism to direct the distal end of the inner catheter for locating and cannulating the patient's coronary sinus. The outer catheter is then longitudinally slid the over the distal end of inner catheter to deep seat the outer catheter within the patient's coronary sinus. The inner catheter is then longitudinally slid out of the proximal end of the catheter assembly to remove the inner catheter. A payload is inserted through the proximal end of the outer catheter such that the payload is inserted into the patient's coronary sinus. The catheter assembly is removed by axially sliding the outer catheter over the payload.

According to another aspect, the method involves providing a catheter assembly further including a steering mechanism disposed within the open lumen of the inner catheter. The steering mechanism includes a guide member and a pull wire. The guide member and the pull wire are extendable beyond the pre-formed distal end of the inner catheter. Locating and cannulating the patient's coronary sinus further involves applying a force to the pull wire to direct the distal end of the inner catheter into the patient's coronary sinus.

The payload used in the method can include a pacing lead. In another aspect, the payload includes an occlusion catheter. Injection of a contrast media through the inner catheter may be done after locating and cannulating the patient's coronary sinus.

The method can further involve inserting a guide wire through a patient's right atrium via an access vessel after providing the catheter assembly. In this case, inserting the distal end of the catheter assembly further involves inserting the distal end of the catheter assembly over the guide wire through the patient's right atrium via an access vessel.

In another embodiment of the present invention, a method of accessing a pulmonary vein of a patient's heart involves providing a catheter assembly. The catheter assembly includes an outer catheter having an open lumen and a pre-formed distal end. An inner catheter having an open lumen and a pre-formed distal end is movably disposed within the open lumen of the outer catheter. The pre-formed distal end of the inner catheter is more flexible than the pre-formed distal end of the outer catheter, and the pre-formed distal end of the inner catheter is extendable beyond the preformed distal end of the outer catheter. A proximal mechanism is included for axially rotating the outer catheter relative to the inner catheter and longitudinally translating the inner catheter relative to the outer catheter. An orientation of the pre-formed distal end of the outer catheter relative to the pre-formed distal end of the inner catheter is modified by relative axial rotation and relative longitudinal translation between the outer and inner catheters such that a distal end of the catheter assembly can assume a selectable plurality of two- and three-dimensional shapes.

The method further involves inserting the distal end of the catheter assembly through a patient's right atrium via an access vessel. A transseptal needle is inserted through an interatrial septum of the patient's heart from the right atrium to create a transseptal puncture into the left atrium. Axially rotating the outer catheter relative to the inner catheter and longitudinally displacing the inner catheter relative to the outer catheter directs the distal end of the catheter assembly for locating and cannulating the transseptal puncture. A payload is inserted through the proximal end of the outer catheter such that the payload is inserted into the pulmonary vein via the left atrium.

In one aspect of the method, the catheter assembly further includes a steering mechanism disposed within the open lumen of the inner catheter. The steering mechanism includes a guide member and a pull wire. The guide member and the pull wire are extendable beyond the pre-formed distal end of the inner catheter. Locating and cannulating the transseptal puncture further involves applying a force to the pull wire to direct the distal end of the catheter assembly into the transseptal puncture.

The payload of the method may include an ablation catheter. The method may also involve injecting a contrast media through the catheter assembly for mapping blood vessels after locating and cannulating the transseptal puncture.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1 is a representative view of a catheter embodying features of the present invention;

FIG. 2 is an axial cross section of a distal end of the catheter corresponding to Section 1-1 in FIG. 1;

FIG. 3 is a view of a distal end of an inner catheter according to one embodiment of the present invention;

FIG. 4 is a view of a distal end of an outer catheter according to one embodiment of the present invention;

FIG. 5 is a view of the distal end shape of the catheter when the inner catheter of FIG. 3 is inserted into the outer catheter of FIG. 4;

FIG. 6 is a view of the catheter distal end shape when the inner catheter of FIG. 3 is extended and rotated within the outer catheter of FIG. 4;

Figure 7:
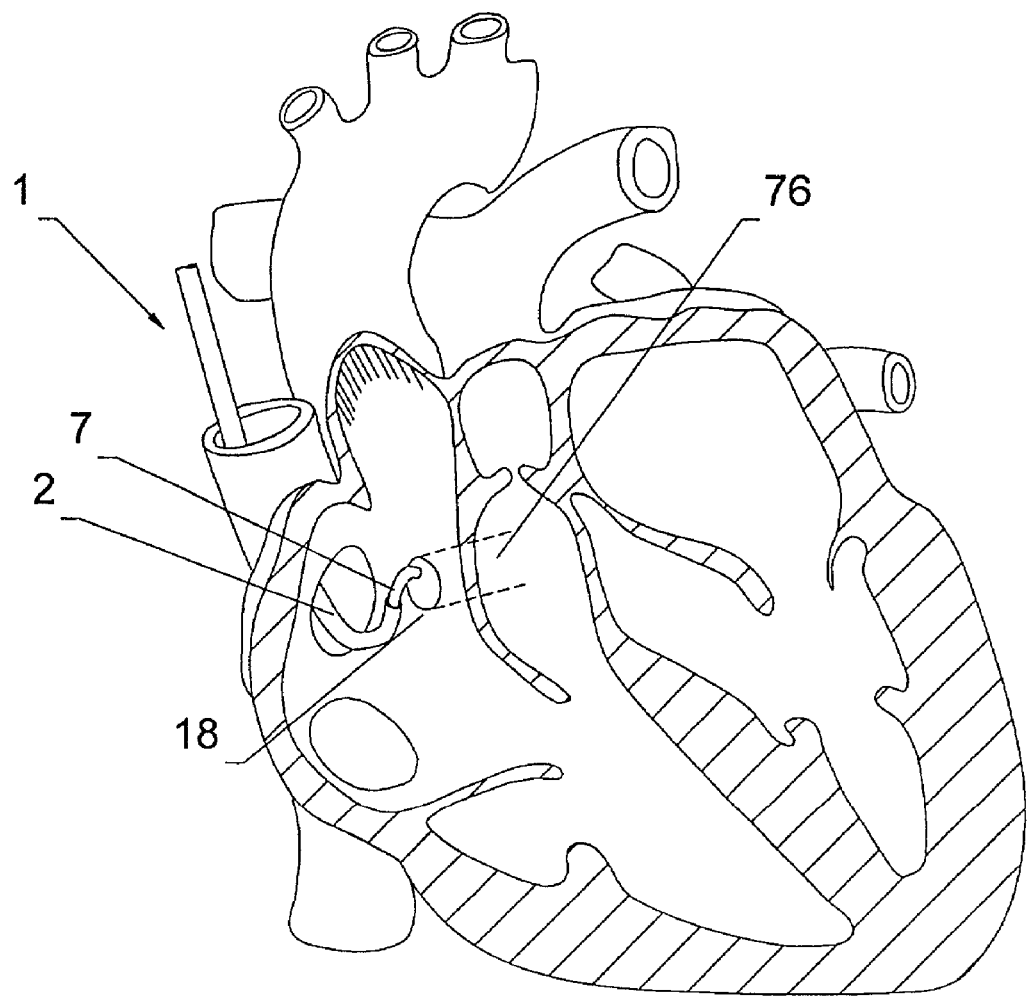
FIG. 7 is a cutaway view of a heart showing the distal tip of the catheter locating the coronary sinus from the right atrium, according to an embodiment of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Referring now to the drawings, and in particular to FIG. 1, there is provided an exterior view of a catheter assembly 1 embodying aspects of the present invention. The catheter assembly 1 includes an outer catheter 2 having an open lumen 3 (best seen in FIG. 2). The outer catheter 2 has a pre-formed curve 4 at a distal end and a proximal mechanism 5. The pre-formed curve 4 can be advantageously shaped and located so that when the outer catheter 2 is advanced to a staging area (e.g. the right atrium), the distal tip 2A of the outer catheter 2 is pointing towards the most probable location of the vessel of interest. The proximal mechanism 5 provides rotational and translational control of the outer catheter 2.

An inner catheter 7 is movably disposed within the open lumen 3 of the outer catheter 2. In the configuration shown in FIG. 1, the inner catheter 7 has a curve 8 pre-formed at or near its distal end and an open lumen 9 (best seen in FIG. 2). The inner catheter 7 can also have adjacent regions of varying bending stiffness along its length. The distal end of the inner catheter 7 is typically more flexible than its proximal end. The distal end of the inner catheter 7 is also typically more flexible than the distal end of the outer catheter 2.

Distal flexibility of the inner catheter 7 can allow the inner catheter 7 to be retracted within the outer catheter 2 without the outer catheter's shape being substantially altered by the pre-formed distal end of the inner catheter 7. In such an arrangement, the distal end of the catheter assembly 1 can take on the approximate shape of the outer catheter 2, this shape being advantageously adapted for advancement to the staging area.

When the outer catheter 2 is advanced and seated in the staging area, the distal tip of the inner catheter 7 can be distally extended from the outer catheter 2. This extension can serve multiple purposes. First, extending the inner catheter 7 lengthens the distal end of the catheter assembly 1 for locating for a vessel of interest. Secondly, this extension allows the distal end of the inner catheter 7 to take on its pre-formed shape once the distal end exits the outer catheter 2. Thirdly, if the inner catheter 7 has been extended sufficiently far, a section of the inner catheter 7 having greater stiffness than the distal end of the inner catheter 7 will be oriented within a substantial length of the pre-formed curve 4 of the outer catheter 2. The pre-formed curve 4 will then straighten by some amount due to increased straightening forces applied by the stiffer part of the inner catheter 7. The amount of straightening depends on the length of the inner catheter's stiffer section that is oriented within the pre-formed curve 4. In this way, distally advancing the inner catheter 7 through the outer catheter 2 can serve to adjustably change the angle of the pre-formed curve 4.

The enlargement of the pre-formed curve 4 by telescoping the inner catheter 7 within the outer catheter 2 gives the physician the useful ability to steer the outer catheter's distal tip 2A, and thereby exercise control over the inner catheter's distal tip 6. Additional control of the inner catheter's distal tip 6 is provided by rotating the inner catheter 7 and outer catheter 2 relative to each other.

Referring now to FIGS. 3 through 6, the advantageous control of catheter tip shape by the relative extension and rotation of inner and outer catheters 7, 2 is illustrated. FIGS. 3 and 4 show possible pre-formed distal shapes of the inner catheter 7 and outer catheter 2, respectively, prior to assembly. In this condition, the inner catheter 7 has a curve 8 with a bend angle 10 and a bend radius 11. The outer catheter 2 has a curve 4 with an initial bend angle 12 and an initial bend radius 13.

FIG. 5 shows the catheters 7 and 2 assembled, with the inner catheter 7 disposed within the outer catheter 2. Once assembled, the distal stiffness of the inner catheter 7 can change the curve 4 to new bend angle 14 and new bend radius 15. Typically, the bend radius 15 is larger than the initial bend radius 13 and the bend angle 14 is smaller than the initial bend angle 12.

In FIG. 6, the inner catheter 7 has been extended such that a stiffer section of the inner catheter 7 extends within the curve 4 of the outer catheter 2. The curve 4 now has new bend angle 16 and new bend radius 17. In this case, the bend radius 17 is larger than both the previous bend radius 15 and the initial bend radius 13. As well, the bend angle 16 is smaller than the previous bend angle 14 and the initial bend angle 12.

Further of interest in FIG. 6, the inner catheter 7 has been rotated relative to the outer catheter 2. The catheter assembly end shapes illustrated in FIGS. 5 and 6 demonstrate how the combination of relative rotation and extension of the catheters 7 and 2 can create a selectable plurality of two- and three-dimensional shapes useful for finding and cannulating a vessel of interest.

With respect to the particular task of finding the coronary sinus of the heart, FIG. 7 is a perspective cutaway view of the heart showing distal ends of the outer catheter 2 and the inner catheter 7 in the right atrium, respectively. The catheter assembly 1 assumes a distal tip shape advantageously providing access to the coronary sinus ostium 18. Once the ostium 18 has been accessed, the inner catheter 7 can be extended distally and deep seated in the coronary sinus 76.

Once the inner catheter 7 has successfully cannulated the destination vessel, the catheter assembly 1 can serve as a guide member for introduction of a payload into the vessel. A payload can be introduced into the proximal end of the catheter assembly and be advanced through one or both of the inner catheter lumen 9 and the outer catheter lumen 3. For purposes of venography, a liquid radiopaque dye may be the payload, the dye being injected through the inner catheter lumen 9 or the outer catheter lumen 3, as appropriate. In another application, an occlusion catheter is a payload that can be advanced through the catheter assembly 1.

Figure 8:
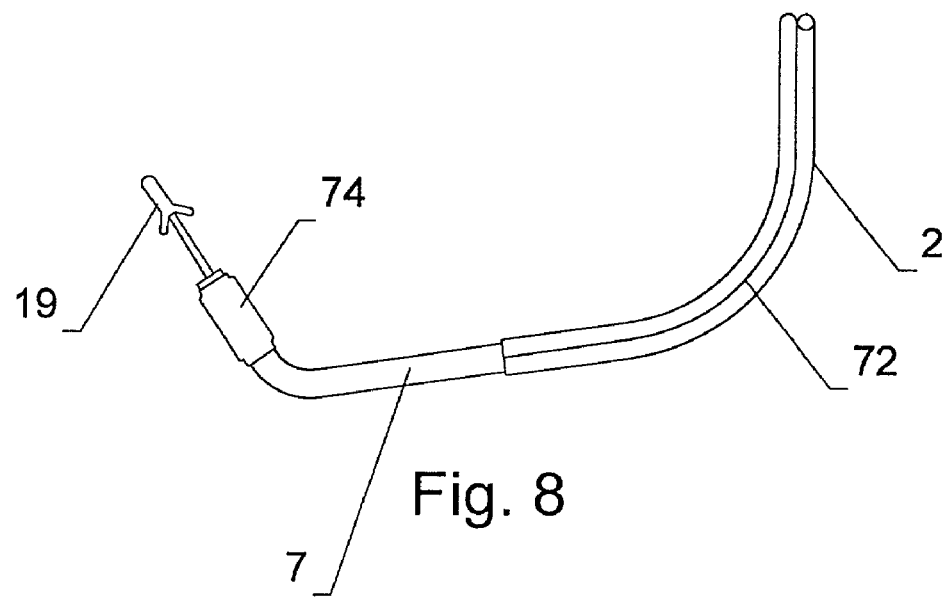
FIG. 8 is an external view showing a pacing lead extending from the distal end of the inner catheter according to one embodiment of the present invention.

A common payload for a catheter according to the present invention is a pacing lead. As shown in FIG. 8, one configuration allows inserting the pacing lead 19 through the inner catheter 7. In some cases, the inner catheter lumen 9 may be too small to pass the pacing lead 19. In such a case, the lead 19 may be passed through the outer catheter 2, as shown in FIG. 9, assuming the inner catheter 7 has been removed prior to advancement of the pacing lead 19 into the outer catheter 2.

To use the outer catheter 2 for guiding the pacing lead 19, the inner catheter 7 is first guided to the destination vessel as previously described. After the destination vessel has been located by the inner catheter 7, the outer catheter 2 can be slid distally over the inner catheter 7 until the outer catheter 2 is seated in the destination vessel. The inner catheter 7 is then proximally retracted and removed from the catheter assembly 1. The outer catheter 2 now serves as a cannulating guide member having a larger lumen 3 through which to pass the pacing lead 19.

Figure 9:
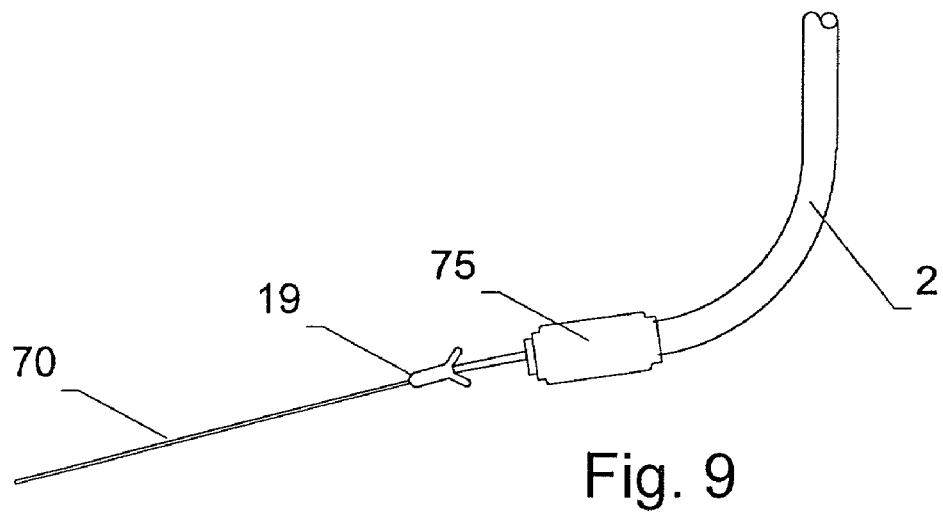
FIG. 9 is a view showing a pacing lead and a guide wire extending from the distal end of the outer catheter according to another embodiment of the present invention.

As seen in FIG. 9, the pacing lead 19 may also be introduced over a guide wire 70. The guide wire 70 may be introduced into the heart before the catheter assembly, serving as a guide and support member into the right atrium, for example. The catheter assembly 1 is then advanced over the guide wire 70. Once the catheter assembly 1 has reached the right atrium, the inner catheter 2 is used to locate and cannulate the vessel of interest. After the vessel of interest has been cannulated, the inner catheter 2 now serves to support the guide wire 70, the guide wire 70 then being advanced into a branch vessel. The pacing lead 19 is then advanced over the guide wire 70 into the branch vessel.

During the procedure of location and cannulation of a heart vessel with the catheter assembly 1, it may be desired to occlude blood flow in a particular blood vessel. The catheter assembly 1 may be adapted for this purpose by attaching an occlusion balloon to the distal end(s) of one or both of the inner and outer catheters 7, 2. An occlusion balloon 74 is shown attached to the inner catheter 7 in FIG. 8. FIG. 9 shows an occlusion balloon 75 attached to the outer catheter 2. The construction and deployment of catheter mounted occlusion balloons is known in the art.

Although the discussion regarding the use of a catheter assembly according to the present invention has been directed to coronary sinus cannulation, it should be understood that the unique navigability provided by such a catheter assembly is not limited to only this application. For example, such a catheter assembly can be used successfully in accessing the left atrium using a transseptal route. In such a procedure, a transseptal (e.g. Brockenbrough) needle can be used to puncture the interatrial septum from the right atrium, after which a guiding catheter is introduced through the puncture into the left atrium. A payload (such as an ablation catheter) can thereby be delivered into the left atrium for treating a variety of conditions, such as atrial fibrillation. A catheter assembly accessing the left atrium can also be used for mapping vessels (e.g. venography) such as the pulmonary vein.

Figure 10:
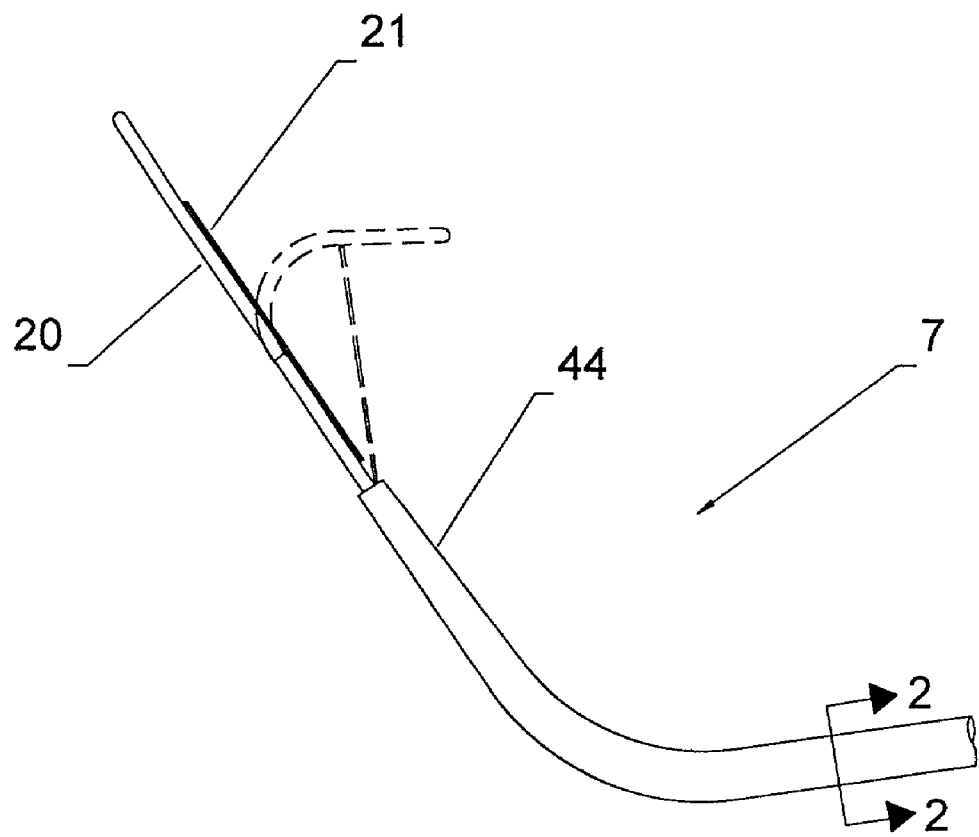
FIG. 10 is a view of the inner catheter with a steering wire and pull wire extending from the distal end of inner catheter according to yet another embodiment of the present invention.

Other adaptations of the invention can provide increased maneuverability of the distal tip of the catheter assembly 1 for accessing vessels that are difficult to reach. Turning now to FIG. 10, a guide member deployed within the inner catheter 7 is shown. The guide member includes a guide wire 20 and a pull wire 21. The pull wire 21 is connected to the guide wire 20 at a point proximal to the distal tip of the guide wire 20. Both wires are movably disposed together within the lumen 9 of the inner catheter 7.

The guide wire 20 and pull wire 21 are accessible from the proximal end of the catheter assembly 1. A tensile force can be applied to the pull wire 21 while the guide wire 20 is held securely. The tensile force acting on the pull wire 21 deflects the tip of the guide wire 20 as shown with phantom lines in FIG. 10. The deflection enables the guide wire 20 to probe for features of interest from the distal end of the inner catheter 7.

The guide wire 20 and pull wire 21 may remain within the distal region of the inner catheter 7, causing deflection of the inner catheter's distal shape.

Figure 11:
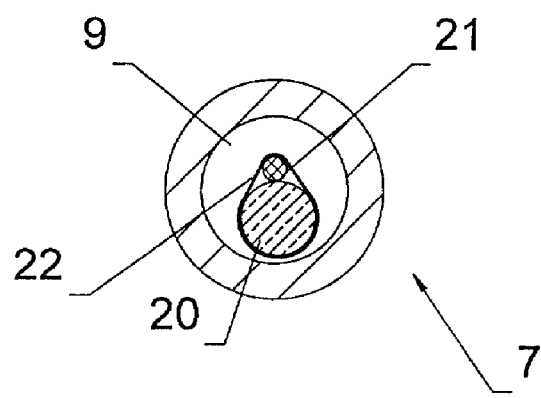
FIG. 11 illustrates Section 2-2 from FIG. 10, showing a cross section of the inner catheter including the steering wire and pull wire.

FIG. 11 is a cross section of the inner catheter 7 showing the guide wire 20 and pull wire 21 disposed within the inner catheter lumen 9. To effectively restrain the pull wire 21 along the length of the guide wire 20, a lubricated sheath 22 may encompass the length of the guide wire 20, except at the proximal and distal ends. The guide wire's distal end is typically left uncovered to allow bending as illustrated in FIG. 11. The guide wire's proximal end is typically left uncovered to enable access for applying separate forces to the guide wire 20 and pull wire 21.

Figure 12:
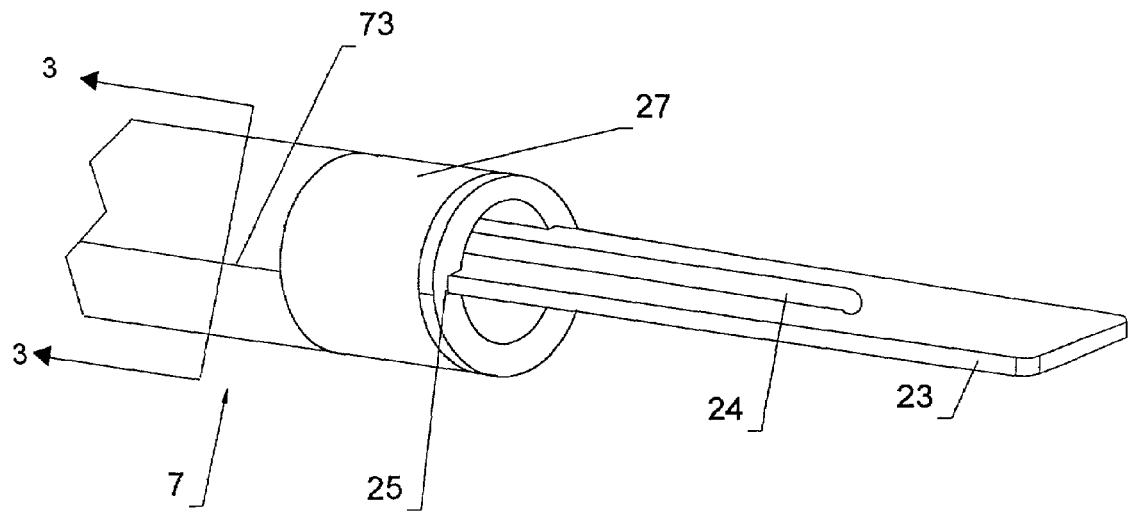
FIG. 12 is a view of the inner catheter with a steering ribbon and pull wire extending from the distal end according to one embodiment of the present invention.

Turning now to FIG. 12, another configuration of the guide member is shown. The guide member includes a guide ribbon 23 and a pull wire 24. The distal end of the guide ribbon 23 is deflected in a manner similar to that described for the guide wire 20 of FIG. 10, e.g. a tensile force applied to the pull wire 24 deflects the distal tip of the guide ribbon 23.

According to this configuration, one or more longitudinal grooves 25 are provided in the inner catheter lumen 9 to restrain relative rotation of the guide ribbon 23. The guide ribbon is slidably disposed within the grooves 25. The longitudinal grooves 25 rotationally limit the guide ribbon 23 with respect to the inner catheter 7. Limiting rotation of the guide ribbon 23 can advantageously restrain the deflection of the guide ribbon 23 to a single, predetermined bending plane.

Figure 13:
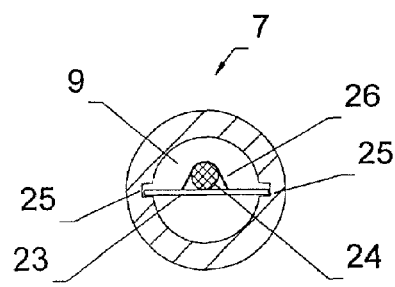
FIG. 13 illustrates Section 3-3 from FIG. 12, showing a cross section of the inner catheter including the steering ribbon and pull wire.

FIG. 13 is a cross section of the inner catheter 7 illustrated in FIG. 12, showing the guide ribbon 23 disposed within the inner catheter lumen 9. In this view, two grooves 25 are shown oppositely disposed within the inner catheter lumen 9. A lubricated sheath 26 may encompass the guide ribbon 23 and pull wire 24 along the length of the guide ribbon 23 to radially restrain the pull wire 24. As with the previously described configuration that uses a guide wire, any sheathing in this configuration would typically exclude coverage of the distal and proximal ends of the guide ribbon 23 to allow proper steering operation.

Various features of a catheter in accordance with the present invention will now be described in greater detail, starting with the inner catheter 7 as shown in FIG. 13. It is understood that the following description of such features is provided for purposes of illustration, and not of limitation. The inner diameter of the inner catheter 7 can range from about 0.035 inches up to about 0.070 inches. The outer diameter can range from about 0.050 inches to about 0.090 inches. The inner catheter 7 may be fabricated from a polymer tube, as typified in the cross section of FIG. 13. A number of polymers are acceptable for the inner catheter construction, including Pebax, nylon, PVC, and polyurethane.

Figure 14:
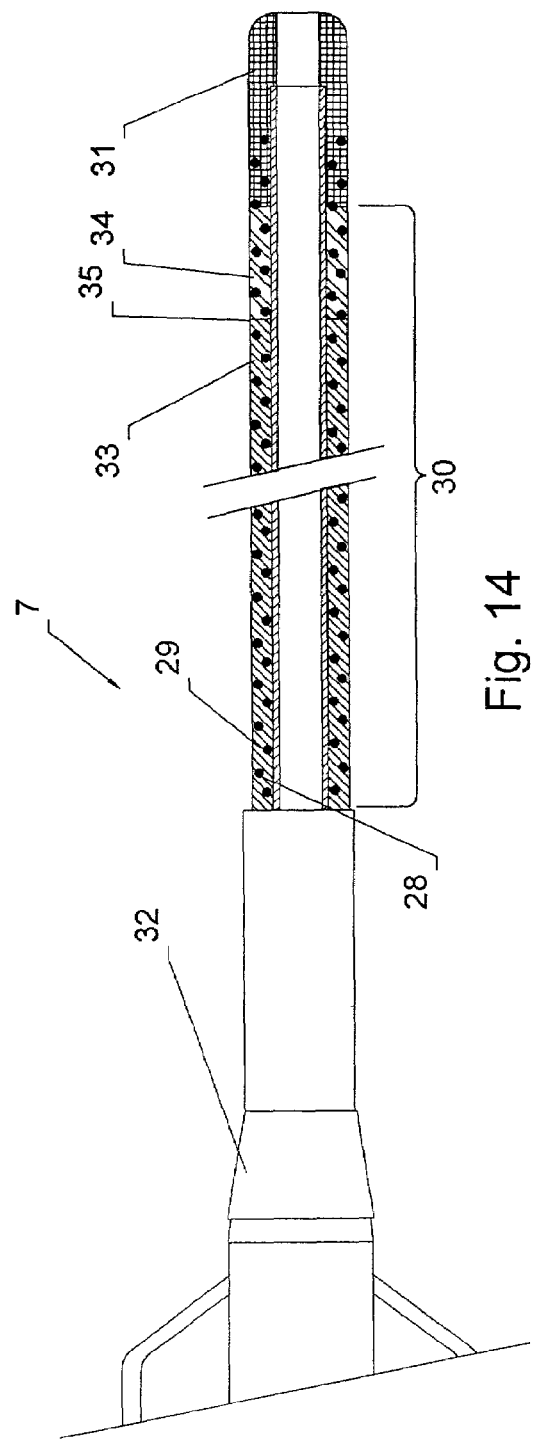
FIG. 14 is a cutaway view of the inner catheter showing tube wall construction and sections of differing stiffness according to one embodiment of the present invention.

In FIG. 14, another configuration of the inner catheter 7 is illustrated in detail. In this configuration, the inner catheter 7 comprises at least three layers—an inner lubricious liner 28, a braid 29, and an exterior jacket 30. The lubricious liner 28 provides a low-friction surface for payloads moving within the inner catheter 7. The lubricious liner 28 may be formed from polytetrafluoroethylene (PTFE) tubing and overlaid with the braid 29. The braid 29 is typically made of stainless steel and helps provide longitudinal stiffness to the inner catheter 7. A stainless steel coil could also be used in place of the braid 29 with similar result.

The exterior jacket 30 provides a smooth outer surface for the inner catheter 7, and can act to further stiffen the inner catheter 7. The exterior jacket 30 may include sections of varying stiffness. In the configuration shown in FIG. 14, two sections of varying stiffness are included, 33 and 34. A stiffness transition 35 occurs at the interface between sections 33 and 34. Section 33 typically has greater stiffness than section 34. The varying stiffness of the sections 33 and 34 can be obtained by using a different durometer polymer material for each section. Other configurations may achieve differing stiffness among sections by varying wall thickness, catheter diameter, or a layout pattern of the braid 29. Typically, the proximal section 33 is jacketed with a Pebax outer lining, and the distal section 34 is jacketed with a lower durometer Pebax material. It is also desirable for the material used to jacket the sections 33, 34 to have a lower durometer rating than the material used to jacket the outer catheter 2. This helps ensure that at least the distal end of the inner catheter 7 is more flexible than the distal end of the outer catheter 2.

The inner catheter 7 may have a soft distal tip 31 that prevents tissue abrasion during introducer procedures. The distal tip 31 is about 1 cm to about 4 cm long, and extends past the lubricious liner 28 and braid 29 on the inner catheter. The distal tip 31 may be composed of a soft polymer.

The inner catheter 7 may also include an attachment 32 at the proximal end that can allow a physician to manipulate the inner catheter 7. One useful attachment 32 is a winged luer, as illustrated in FIG. 14. The end attachment 32 is typically secured to the proximal end of the outer jacket 30 and/or the stainless steel braid 29.

The inner catheter length usually ranges from about 55 cm to about 80 cm. Typically, the inner catheter 7 is at least about 13 cm longer than the outer catheter 2. The stiffness transition 35 can be located from about 5 cm to about 20 cm from the distal end of the inner catheter 7.

The inner catheter 7 may have a curve 8 pre-formed at the distal end, as is best seen in FIG. 1. In one configuration, the curve 8 includes a circular bend with a radius defined from an inner bend surface of the inner catheter. The radius is about 0.5 cm to about 5.0 cm. The bend also includes an arc angle ranging between about 20 degrees to about 270 degrees.

Figure 15:
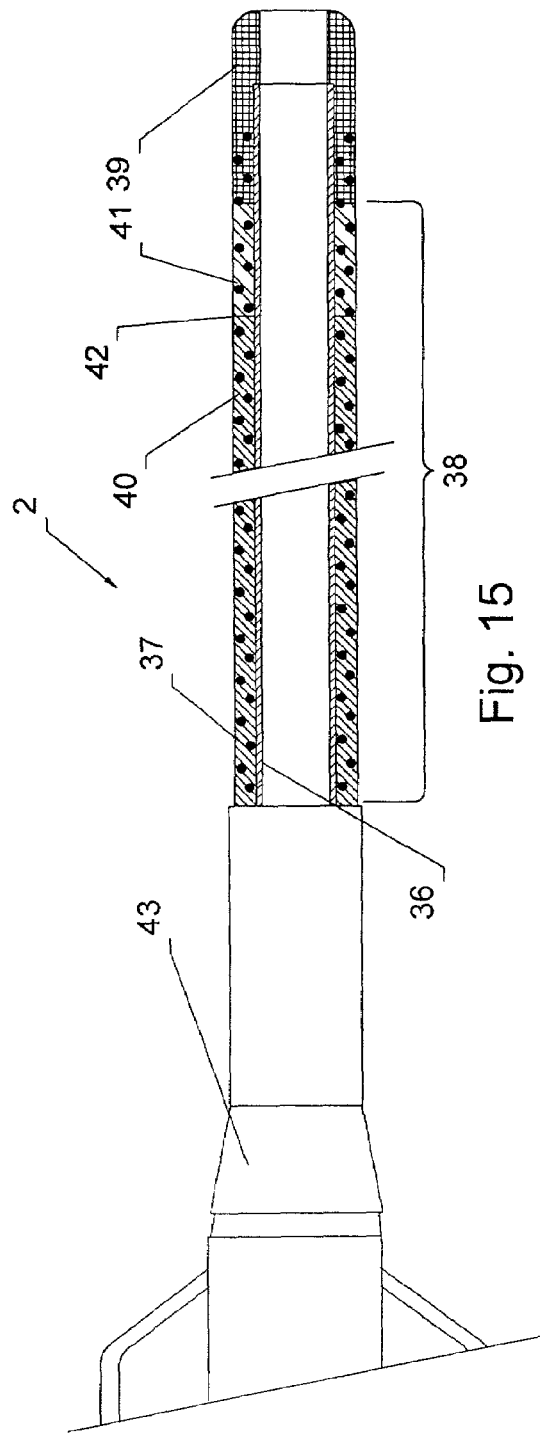
FIG. 15 is a cutaway view of the outer catheter showing tube wall construction and sections of differing stiffness according to one embodiment of the present invention.

Turning now to FIG. 15, a configuration of the outer catheter 2 is detailed. Although the outer catheter 2 can be constructed from a single polymeric tube, in this configuration the outer catheter 2 is formed of a multi-layer tube. As with the inner catheter 7 shown in FIG. 14, the tube includes at least three layers—an inner lubricious liner 36, a braid 37, and an exterior jacket 38. The lubricious liner 36 provides a low-friction surface for the inner catheter 7 moving within the outer catheter 2, and can be formed of PTFE. The braid 37 is usually made of stainless steel and provides longitudinal stiffness to the outer catheter 2. The exterior jacket 38 provides a smooth outer surface for the outer catheter 2, and can act to further stiffen the outer catheter 2.

The outer catheter 2 may have a soft distal tip 39, which prevents tissue abrasion during introducer procedures. The outer catheter 2 may have an end attachment 43 at the proximal end to at least allow a physician to manipulate the outer catheter 2. The end attachment 43 can be a winged luer such as illustrated in FIG. 15. The end attachment 7 is typically secured to the proximal end of the exterior jacket 38 or stainless steel braid 37, and may also include a hemostatic valve to seal the proximal end of the inner catheter 7 within the outer catheter 2.

As with the inner catheter 7, the exterior jacket 38 of the outer catheter 2 may include sections of varying stiffness. In the outer catheter 7 shown in FIG. 15, two sections of varying stiffness are included, 40 and 41. A stiffness transition 42 occurs at the interface between sections 40 and 41. Section 40 typically has greater stiffness than section 41. The varying stiffness of the sections 40 and 41 can be obtained by forming the exterior jacket 38 at each section from a different durometer material. Pebax is typically the material of choice for the jacket 38, although other polymers such as nylon may also suffice. Other embodiments may achieve differing stiffness among sections by changing wall thickness or a layout pattern of the braid 37.

The typical outer diameter of the outer catheter 2 is about 0.100 inches to about 0.110 inches. The inner diameter ranges from about 0.055 inches to about 0.90 inches. The inner diameter of the outer catheter 2 is usually designed to be at least about 0.002 inches larger than the outer diameter of the associated inner catheter 7 to allow relative motion between the catheters 2, 7. The length of the outer catheter ranges from about 35 cm to about 60 cm in typical configurations. The transition 42 between the sections 40 and 41 is located about 5 cm to about 20 cm from the distal tip of the outer catheter 2.

In one useful configuration, the outer catheter 2 may be constructed with a peel-away feature. Referring again to FIG. 8, this feature may include one or more longitudinal pre-stress lines 72 running from proximal to distal ends of the outer catheter 2. The pre-stress line(s) 72 can include a void or channel in the wall of the outer catheter 2 that weaken the outer catheter wall, thereby easing peel-away separation. The inner catheter 7 may include a similar peel-away feature. Inner catheter pre-stress lines 73 are shown in FIG. 12.

Figure 16:
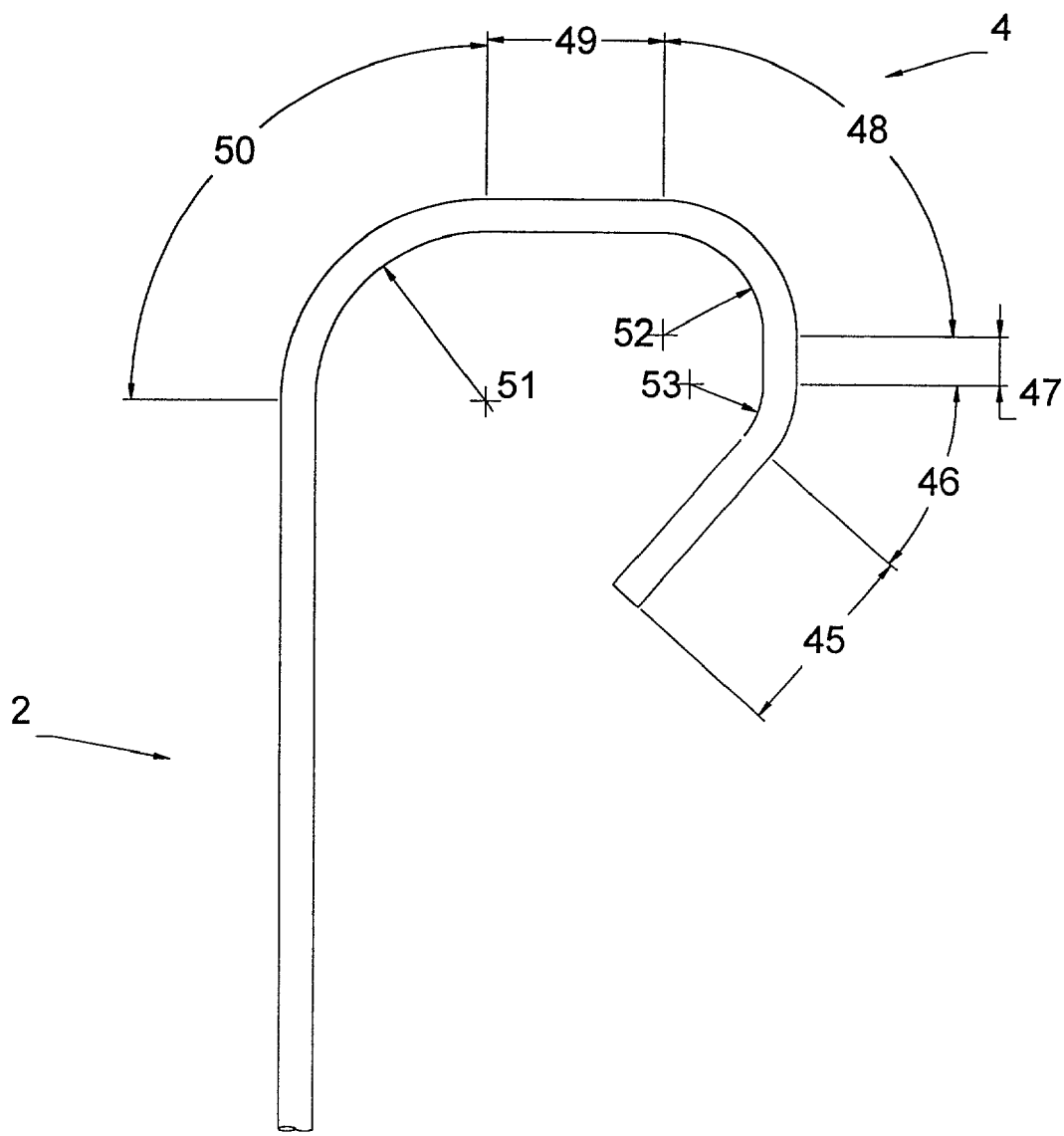
FIG. 16 is a view of one configuration of the outer catheter's distal curve.

Turning now to FIG. 16, a useful pre-formed curve 4 shape on the outer catheter 2 is illustrated. In all descriptions of circular curve features that follow, bend radius is measured from the exterior of the outer catheter 2 relative to an inner surface of the bend, and bend angle is the arc angle traversed by the curve. In the configuration shown in FIG. 16, the curve 4 includes a first straight section 45 at the distal tip with a length ranging from about 0 cm to about 6 cm. Adjacent to the first straight section 45 is a first curve 46 having a substantially circular shape with a bend angle ranging from about 0 degrees to about 80 degrees and a bend radius 53 ranging from about 1 cm to about 5 cm. Adjacent to the first curve 46 is a second straight section 47 having a length ranging from about 0 cm to about 6 cm. Adjacent to the second straight section 47 is a second curve 48 having a substantially circular shape with a bend angle ranging from about 0 degrees to about 100 degrees and a bend radius 52 ranging from about 1 cm to about 5 cm. Adjacent to the second curve 48 is a third straight section 49 having a length ranging from about 0 cm to about 6 cm. Finally, adjacent to the third straight section 49 is a third curve 50 having a substantially circular shape with a bend angle ranging from about 0 degrees to about 125 degrees and a bend radius 51 ranging from about 1 cm to about 5 cm.

Figures 17, 18:
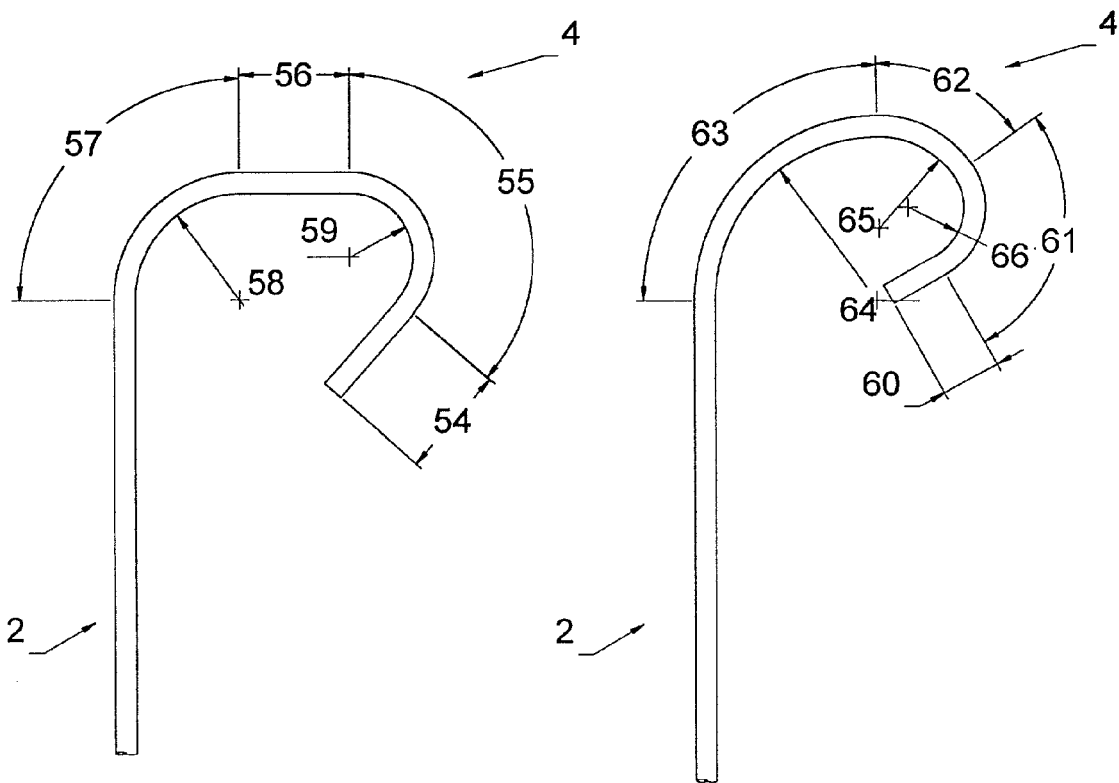
FIG. 17 is a view of another configuration of the outer catheter's distal curve.
FIG. 18 is a view of a further configuration of the outer catheter's distal curve.
Figure 19:
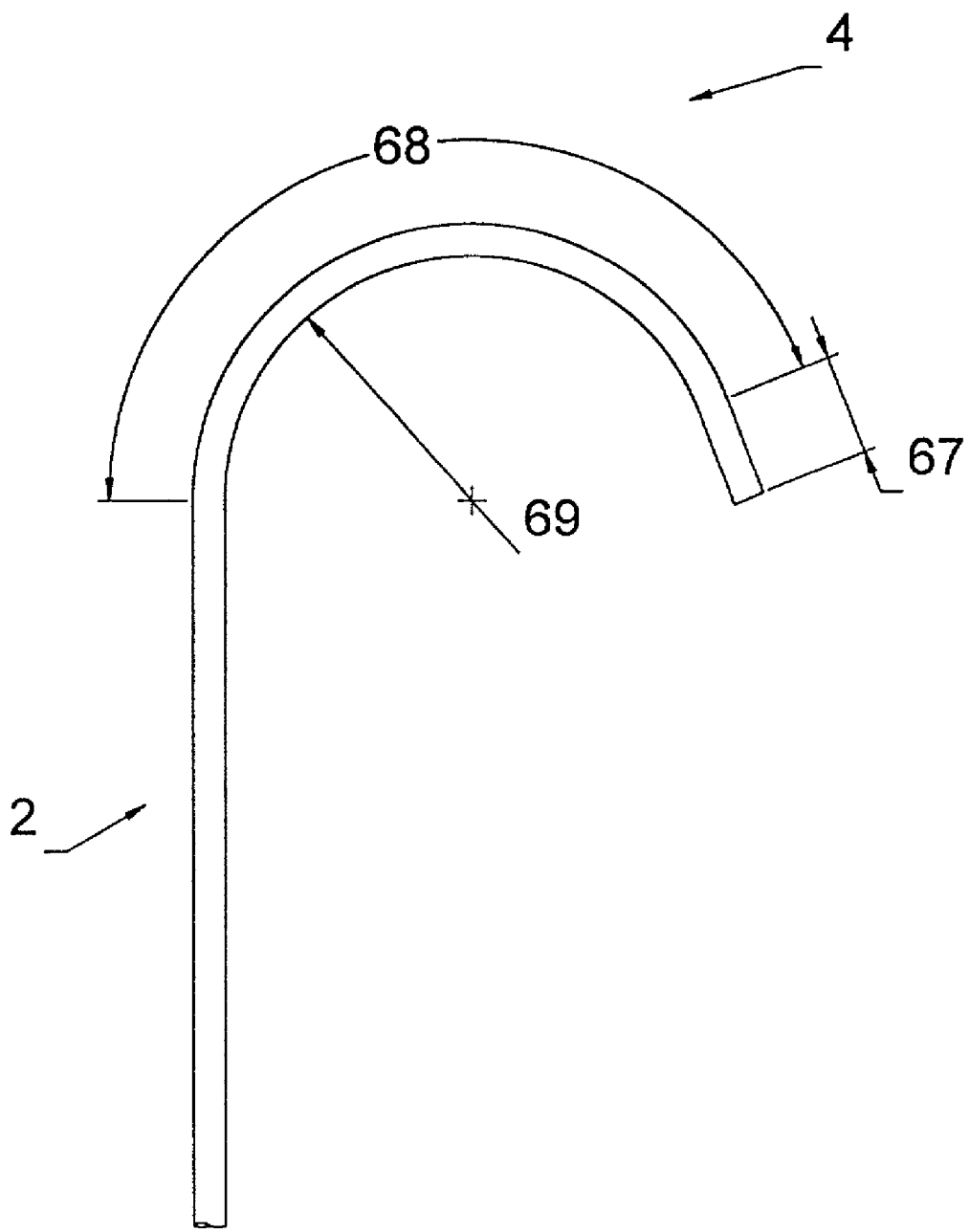
FIG. 19 is a view of yet another configuration of the outer catheter's distal curve.

Other variations of a pre-formed curve 4 are particularly useful, and are illustrated in FIGS. 17 through 19. With respect to FIG. 17, the curve 4 includes a first straight section 54 at the distal tip with a length ranging from about 0 cm to about 6 cm. Adjacent to the first straight section 54 is a first curve 55 having a substantially circular shape with a bend angle ranging from about 0 degrees to about 180 degrees and a bend radius 59 ranging from about 1 cm to about 5 cm. Adjacent to the first curve 55 is a second straight section 56 having a length ranging from about 0 to about 6 cm. Adjacent to the second straight section 56 is a second curve 57 having a substantially circular shape with a bend angle ranging from about 0 degrees to about 125 degrees and a bend radius 58 ranging from about 1 cm to about 5 cm.

FIG. 18 illustrates a curve 4 with a first straight section 60 at the distal tip with a length ranging from about 0 cm to about 6 cm. Adjacent to the first straight section 60 is a first curve 61 having a substantially circular shape with a bend angle ranging from about 0 degrees to about 80 degrees and a bend radius 59 ranging from about 1 cm to about 5 cm. Adjacent to the first curve 61 is a second curve 62 having a substantially circular shape with a bend angle ranging from about 0 degrees to about 100 degrees and a bend radius 58 ranging from about 1 cm to about 5 cm. Adjacent to the second curve 62 is a third curve 63 having a substantially circular shape with a bend angle ranging from about 0 degrees to about 125 degrees and a bend radius 64 ranging from about 1 cm to about 5 cm.

FIG. 19 illustrates a curve 4 with a straight section 67 at the distal tip with a length ranging from about 0 cm to about 6 cm. Adjacent to the straight section 67 is a curve 68 having a substantially circular shape with a bend angle ranging from about 0 degrees to about 180 degrees and a bend radius 69 ranging from about 1 cm to about 5 cm.

The inner catheter 7 may also include a pre-formed curve 8 having features similar to that of curve 4 described with regard to the outer catheter 2.

Other configurations of the catheter assembly 1 may include additional features that add functionality for uses beyond guiding applications. For obtaining ECG readings from areas such as the heart, for example, electrodes may be added to the distal end of one or both of the inner and the outer catheters 7, 2. ECG electrodes are typically made of stainless steel, although other materials such as platinum and silver are known to work in this application. Further, ablation electrodes can be similarly deployed on the catheters 7, 2. Ablation electrodes are commonly made from platinum/iridium.

Turning again to FIG. 12, an end electrode 27 is shown located at the distal tip of the inner catheter 7. Alternate arrangements can employ an electrode at the distal tip of the outer catheter 2, as well as a plurality of band electrodes arrayed along the distal end of at least one of the inner catheter 7 and outer catheter 2. The electrode 27 is typically flush mounted and can be embedded in or bonded to the wall of the catheter 2, 7. Conductors 71 (best seen in FIG. 2) are connected to the electrode 27 to carry electrical signals to and from the electrode 27 to the distal end of the catheter assembly 1. Conductors 71 may be soldered or welded to the electrode 27.

The conductors 71 are disposed within one or both of the inner and outer catheters 7, 2, and exit the proximal end of the catheter assembly 1. In the configuration shown in FIG. 2, the conductors 71 are embedded in the tubular walls of one or both of the inner and outer catheters 7, 2. In other configurations, the conductors are disposed through one or both of the inner and outer catheter lumens 9, 3.

A catheter assembly according to the present invention can be utilized in various ways. One application involves a method of accessing the coronary sinus. The method involves inserting the distal tip of the catheter assembly 1 through an incision to a percutaneous access vessel, e.g. a vessel externally accessed through the skin. Common access vessels include the right and left cephalic veins, the subclavian vein, and the internal jugular vein.

Referring again to FIG. 9, a guide wire 70 is often introduced through the access vessel into the right atrium. The catheter can then be advanced over the guide wire 70 into the right atrium through the superior vena cava, for example. The guide wire 70 is frequently used to probe for venous obstructions up to the superior vena cava, and may be further advanced, if possible, into the coronary sinus ostium. More typically, the catheter assembly 1 is deployed over the guide wire 70, the guide wire 70 helping to provide support and guidance for the catheter assembly as it is advanced into the right atrium. From the right atrium, the catheter assembly 1 can then effectively locate and cannulate the coronary sinus, and thereby provide a conduit for the guide wire 70 into the coronary sinus.

Once the distal end of the catheter assembly 1 is in the right atrium, the inner catheter 7 can be longitudinally extended via a proximal mechanism 5 to locate the coronary sinus ostium. To aid in locating the ostium, the outer catheter 2 can be rotated relative to the inner catheter 7, allowing the distal end of the catheter assembly 1 to take on various shapes.

After the inner catheter 7 locates the coronary sinus ostium, the outer catheter 2 can be slid over the inner catheter 7 until the outer catheter 2 is deep seated in the coronary sinus. The inner catheter 7 can then be removed by proximally sliding out of the catheter assembly.

Following the outer catheter 2 being seated in the coronary sinus, the outer catheter 2 can be used to introduce a payload into the heart. With reference to FIG. 9, the payload may be a pacing lead 19. If the guide wire 70 was utilized, the guide wire can be advanced past the outer catheter 2 into a branch of the coronary sinus. The pacing lead 19 is then introduced over the guide wire and through the outer catheter 2 until it is seated in a branch of the coronary sinus.

Once the payload has been successful seated, the outer catheter 2 can then be removed. Assuming the payload is to remain in the heart, the outer catheter 2 is slid in a proximal direction over the payload until the outer catheter 2 is removed from the access vessel. If the guide wire 70 was used, it may also be removed.

In one aspect of the present invention, the method of accessing a vessel of interest can involve a steering mechanism disposed within the inner catheter, as shown in FIG. 10, for example. The steering mechanism includes a pull wire 21 and a steering member 20. When the distal end of the catheter assembly 1 is in the right atrium, the steering mechanism can further assist in guiding the distal end of the inner catheter 2 to the intended destination.

It will, of course, be understood that various modifications and additions can be made to the preferred embodiments discussed hereinabove without departing from the scope of the present invention. For example, although the present invention is particularly useful in providing percutaneous access to the coronary sinus ostium via the right atrium, it can be appreciated by one skilled in the art that the present invention is useful in a multitude of guiding catheter applications. Accordingly, the scope of the present invention should not be limited by the particular embodiments described above, but should be defined only by the claims set forth below and equivalents thereof.

What is claimed is:

1. A catheter assembly for cannulating the coronary sinus of a patient's heart from the right atrium, comprising:
    an outer catheter comprising an open lumen and a pre-formed distal end having a plurality of curved sections and a generally straight distal tip section, all of the curved sections in the pre-formed distal end being oriented so as to assume the same general direction of curvature, the generally straight distal tip section extending from a distal-most curved section in a direction defined by the curvature of the distal-most curved section;
    an inner catheter comprising an open lumen and a pre-formed distal end having an open distal tip, the pre-formed distal end including at least two adjacent longitudinal sections of varying stiffness and a stiffness transition region between the at least two adjacent longitudinal sections of varying stiffness, at least a portion of the inner catheter including a braid covered by an exterior jacket, the inner catheter movably disposed within the open lumen of the outer catheter, the pre-formed distal end of the inner catheter being more flexible than the pre-formed distal end of the outer catheter, and the pre-formed distal end of the inner catheter extendable beyond the preformed distal end of the outer catheter; and
    a proximal mechanism for axially rotating the outer catheter relative to the inner catheter and longitudinally translating the inner catheter relative to the outer catheter, an orientation of the pre-formed distal end of the outer catheter relative to the pre-formed distal end of the inner catheter modified by relative axial rotation and relative longitudinal translation between the outer and inner catheters such that one or both of a bend radius and a bend angle of the pre-formed distal end of the outer catheter is modified and a distal end of the catheter assembly can assume a selectable plurality of multidimensional shapes appropriate for accessing the coronary sinus.

2. A catheter assembly according to claim 1, wherein the pre-formed distal end of the outer catheter further comprises:
    at least two adjacent longitudinal sections of varying stiffness; and
    at stiffness transition region between the at least two adjacent longitudinal sections of varying stiffness.

3. A catheter assembly according to claim 1, wherein the pre-formed distal end of the inner catheter includes a taper.

4. A catheter assembly according to claim 1, wherein the inner catheter is disposed within the open lumen of the outer catheter such that the distal end of the inner catheter protrudes from about 3 cm to about 15 cm from a distal tip of the outer catheter.

5. A catheter assembly according to claim 1, wherein the pre-formed distal end of the inner catheter further comprises one or more substantially straight sections adjacent one or more curved sections.

6. A catheter assembly according to claim 1, wherein the pre-formed distal end of the inner catheter further comprises at least one bend with a bend radius ranging from about 0.5 cm to about 5.0 cm and a bend angle ranging from about 0 degrees to about 180 degrees.

7. A catheter assembly according to claim 1, wherein the pre-formed distal end of the outer catheter further comprises one or more substantially straight sections adjacent one or more of the plurality of curved sections.

8. A catheter assembly according to claim 1, wherein:
    the generally straight distal tip section of the outer catheter has a length of about 0 cm to about 6 cm; and
    the pre-formed distal end of the outer catheter comprises:
    a first curve proximally adjacent to the distal tip section having a bend radius of about 1 cm to about 5 cm and a bend angle of about 0 degrees to about 80 degrees;
    a second straight section proximally adjacent to the first curve having a length of about 0 cm to about 6 cm; and
    a second curve proximally adjacent to the second straight section having a bend radius of about 1 cm to about 5 cm and a bend angle of about 0 degrees to about 100 degrees.

9. A catheter assembly according to claim 8, wherein the pre-formed distal end of the outer catheter further comprises:
    a third straight section proximally adjacent to the second curve having a length of about 0 cm to about 6 cm; and
    a third curve proximally adjacent to the third straight section having a bend radius of about 1 cm to about 5 cm and a bend angle of about 0 degrees to about 125 degrees.

10. A catheter assembly according to claim 1, further comprising a steering mechanism disposed within an open lumen of the inner catheter, the steering mechanism comprising a guide member and a pull wire, the guide member and the pull wire extendable beyond the pre-formed distal end of the inner catheter.

11. A catheter assembly according to claim 10, wherein a bend at a distal section of the guide member is developed upon application of a force to the pull wire.

12. A catheter assembly according to claim 10, wherein the distal end of the catheter assembly assumes a plurality of two- and three-dimensional shapes in response to axial rotation and longitudinal transition of the outer catheter relative to the inner catheter and application of force to the pull wire.

13. A catheter assembly according to claim 10, wherein the guide member comprises a guide wire.

14. A catheter assembly according to claim 10, wherein the guide member comprises a guide ribbon.

15. A catheter assembly according to claim 14, wherein the inner catheter further comprises longitudinal slots disposed along an open lumen of the inner catheter, the guide ribbon slidably disposed within the longitudinal slots of the inner catheter.

16. A catheter assembly according to claim 1, further comprising:
    at least one electrode located on the distal end of at least one of the inner and outer catheters; and
    an electrical conductor coupled to the at least one electrode, the conductor disposed within at least one of the inner and outer catheters.

17. A catheter assembly according to claim 1, further comprising an occlusion balloon connected to the distal end of the inner catheter.

18. A catheter assembly according to claim 17, wherein the pre-formed distal end of the outer catheter further comprises:
    at least two adjacent longitudinal sections of varying stiffness; and
    a stiffness transition region between the at least two adjacent longitudinal sections of varying stiffness.

19. A catheter assembly according to claim 1, further comprising an occlusion balloon connected to the distal end of the outer catheter.

20. A catheter assembly, comprising:
    an outer catheter comprising an open lumen and a pre-formed distal end having a plurality of curved sections and a generally straight distal tip section, all of the curved sections in the pre-formed distal end being oriented so as to assume the same general direction of curvature, the generally straight distal tip section extending from a distal-most curved section in a direction defined by the curvature of the distal-most curved section;
    an inner catheter having an open lumen, a pre-formed distal end having an open distal tip, at least two adjacent longitudinal sections of varying stiffness, and a stiffness transition region between the at least two adjacent longitudinal sections of varying stiffness, at least a portion of the inner catheter including a braid covered by an exterior jacket, the inner catheter movably disposed within the open lumen of the outer catheter, the pre-formed distal end of the inner catheter being more flexible than the pre-formed distal end of the outer catheter, and the pre-formed distal end of the inner catheter extendable beyond the preformed distal end of the outer catheter; and
    a proximal mechanism for axially rotating the outer catheter relative to the inner catheter and longitudinally translating the inner catheter relative to the outer catheter, an orientation of the pre-formed distal end of the outer catheter relative to the pre-formed distal end of the inner catheter modified by relative axial rotation and relative longitudinal translation between the outer and inner catheters and a shape of the pre-formed distal end of the outer catheter changed by relative longitudinal translation between the outer and inner catheters thereby changing orientation of the sections of varying stiffness of the inner catheter relative to the pre-formed distal end of the outer catheter, such that a distal end of the catheter assembly can assume a selectable plurality of multidimensional shapes.

21. A catheter assembly according to claim 20, wherein the pre-formed distal end of the inner catheter is tapered.

22. A catheter assembly according to claim 20, wherein the stiffness transition region of the inner catheter is about 5 cm to about 20 cm from a distal tip of the inner catheter.

23. A catheter assembly according to claim 20, wherein the pre-formed distal end of the inner catheter comprises a bend having a bend radius ranging from about 0.5 cm to about 5.0 cm and a bend angle ranging from about 0 degrees to about 180 degrees.

24. A catheter assembly according to claim 20, wherein the pre-formed distal end of the outer catheter further comprises one or more substantially straight sections adjacent one or more of the plurality of curved sections.

25. A catheter assembly according to claim 20, wherein:
    the generally straight distal tip section of the outer catheter has a length of about 0 cm to about 6 cm; and
    the pre-formed distal end of the outer catheter comprises:
    a first curve proximally adjacent to the distal tip section having a bend radius of about 1 cm to about 5 cm and a bend angle of about 0 degrees to about 80 degrees;
    a second straight section proximally adjacent to the first curve having a length of about 0 cm to about 6 cm; and
    a second curve proximally adjacent to the second straight section having a bend radius of about 1 cm to about 5 cm and a bend angle of about 0 degrees to about 100 degrees.

26. A catheter assembly according to claim 25, wherein the pre-formed distal end of the outer catheter further comprises:
    a third straight section proximally adjacent to the second curve having a length of about 0 cm to about 6 cm; and
    a third curve proximally adjacent to the third straight section having a bend radius of about 1 cm to about 5 cm and a bend angle of about 0 degrees to about 125 degrees.

* * * * *